(12) United States Patent
Dannelongue

(10) Patent No.: US 9,275,482 B1
(45) Date of Patent: Mar. 1, 2016

(54) DISPLAY SELECTION BASED ON DATA FORMAT RECOGNITION

(75) Inventor: Herve Dannelongue, Belmont, MA (US)

(73) Assignee: The MathWorks, Inc., Natick, MA (US)

( * ) Notice: Subject to any disclaimer, the term of this patent is extended or adjusted under 35 U.S.C. 154(b) by 796 days.

(21) Appl. No.: 13/078,725

(22) Filed: Apr. 1, 2011

(51) Int. Cl.
*G06T 11/20* (2006.01)
*G06F 19/00* (2011.01)

(52) U.S. Cl.
CPC .......... *G06T 11/206* (2013.01); *G06F 19/708* (2013.01)

(58) Field of Classification Search
CPC .................................................. G06T 11/206
USPC .......................................................... 345/440
See application file for complete search history.

(56) References Cited

U.S. PATENT DOCUMENTS

| | | | | |
|---|---|---|---|---|
| 5,581,678 | A * | 12/1996 | Kahn ............................. | 345/440 |
| 7,487,077 | B1 * | 2/2009 | Clune et al. ..................... | 703/17 |
| 7,509,244 | B1 * | 3/2009 | Shakeri et al. ................... | 703/7 |
| 2003/0004992 | A1 * | 1/2003 | Matsui et al. .................. | 707/512 |
| 2004/0027452 | A1 * | 2/2004 | Yun et al. ........................ | 348/51 |
| 2004/0176948 | A1 * | 9/2004 | Oh et al. ........................ | 704/201 |
| 2005/0278162 | A1 * | 12/2005 | Ciolfi et al. ..................... | 703/22 |
| 2006/0026318 | A1 * | 2/2006 | Lee ................................. | 710/72 |
| 2006/0056680 | A1 * | 3/2006 | Stutsman et al. ............. | 382/154 |
| 2007/0100520 | A1 * | 5/2007 | Shah et al. ....................... | 701/33 |
| 2008/0303832 | A1 * | 12/2008 | Kim et al. ...................... | 345/501 |

OTHER PUBLICATIONS

The MathWorks, Inc., "Imfinfo", Information about graphics file—MATLAB, http://www.mathworks.com/help/techdoc/ref/imfinfo.html, Jan. 6, 2011, 2 pages.
Wikipedia, "File format", http://en.wikipedia.org/wiki/File_format, Feb. 26, 2011, 9 pages.
MKS Inc., "File—determine file type", http://www.mkssoftware.com/docs/man1/file.1.asp, Feb. 28, 2011, 2 pages.

* cited by examiner

*Primary Examiner* — Ke Xiao
*Assistant Examiner* — Kyle Zhai
(74) *Attorney, Agent, or Firm* — Harrity & Harrity, LLP

(57) ABSTRACT

A method may include receiving a selection of a streaming data source, where the streaming data source provides data to a display component in a graphical model; determining a data type for the data associated with the streaming data source. Determining the data type may include reading a portion of the data from the data source, analyzing the read data portion to determine a data pattern, and identifying the data type based on the data pattern, where the identified data type is one of a plurality of available data types. The method may further include selecting, in response to determining the data type, a visual representation for the data associated with the data source; and displaying the data associated with the data source using the selected visual representation within the display component.

20 Claims, 13 Drawing Sheets

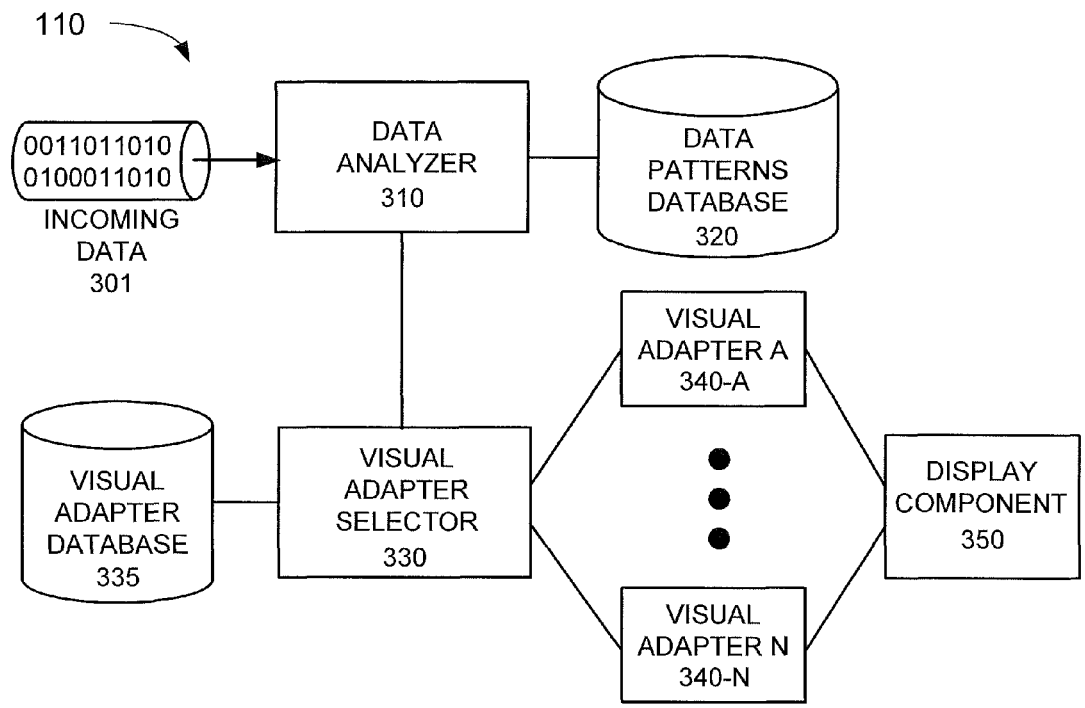
FIG. 3
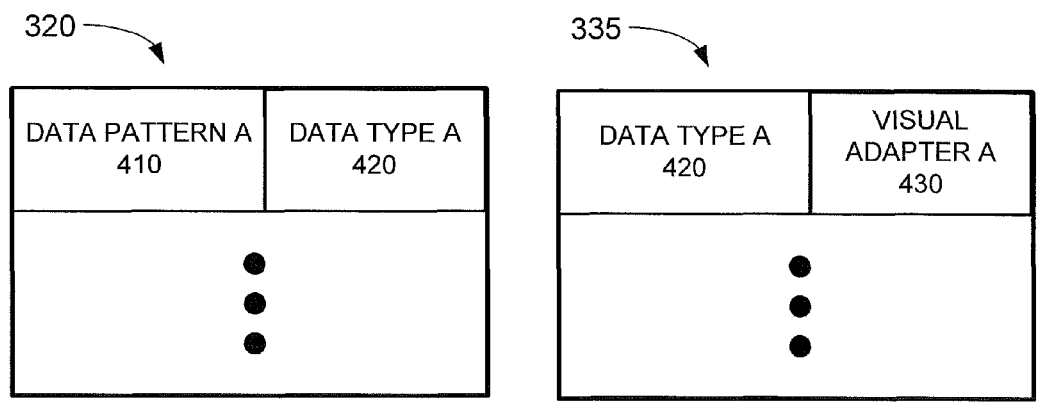
FIG. 4A  FIG. 4B

DISPLAY SELECTION BASED ON DATA FORMAT RECOGNITION

BACKGROUND INFORMATION

When a user interacts with a computer device, the user may request to open a particular file or a data stream. The requested file or data stream may be associated with a particular application or a particular format. In order to select a correct application or a correct format, the user may be prompted by the computer device to select an application or a format from a list. Having to select an application or format from a list may prove to be cumbersome and/or confusing for a user, especially when the user is provided with multiple applications or formats from which to choose. Furthermore, a user may not know how to select an application or format for a file or a data stream.

BRIEF DESCRIPTION OF THE DRAWINGS

FIG. 3 is a diagram of example functional components of a computer device according to an implementation described herein;

FIG. 4A is a diagram of example fields that may be stored in a data patterns database according to an implementation described herein;

FIG. 4B is a diagram of example fields that may be stored in a visual adapter database according to an implementation described herein;

DETAILED DESCRIPTION OF PREFERRED EMBODIMENTS

The following detailed description refers to the accompanying drawings. The same reference numbers in different drawings identify the same or similar elements. Also, the following detailed description does not limit the invention.

An implementation described herein may relate to display selection for a data source based on data format recognition. Conventional techniques may prompt a user to indicate a data type for a data source or to select a display type for the data source. In contrast, the implementation may programmatically select a display type and/or visual representation for data associated with the data source absent input from the user. The data source may include a locally or remotely stored file or data being streamed from a local or remote device.

In one example, the display type and/or visual representation may be selected based on a file extension or file header associated with the data source. In another example, the display type and/or visual representation may be selected based on a data pattern associated with the data source. For example, a data sample may be extracted from the data source, where the data sample includes a portion of the data residing in the data source. The data sample may be analyzed for a data pattern. The analyzed data pattern may be compared to a list of data patterns associated with particular data types, and a data type may be selected based on the comparison. A visual representation of data associated with the data source may be generated and displayed based on the selected data type. Steps in the above example may be performed without requiring that a user select a data type or a visual representation for data in the data source.

Figure 1:
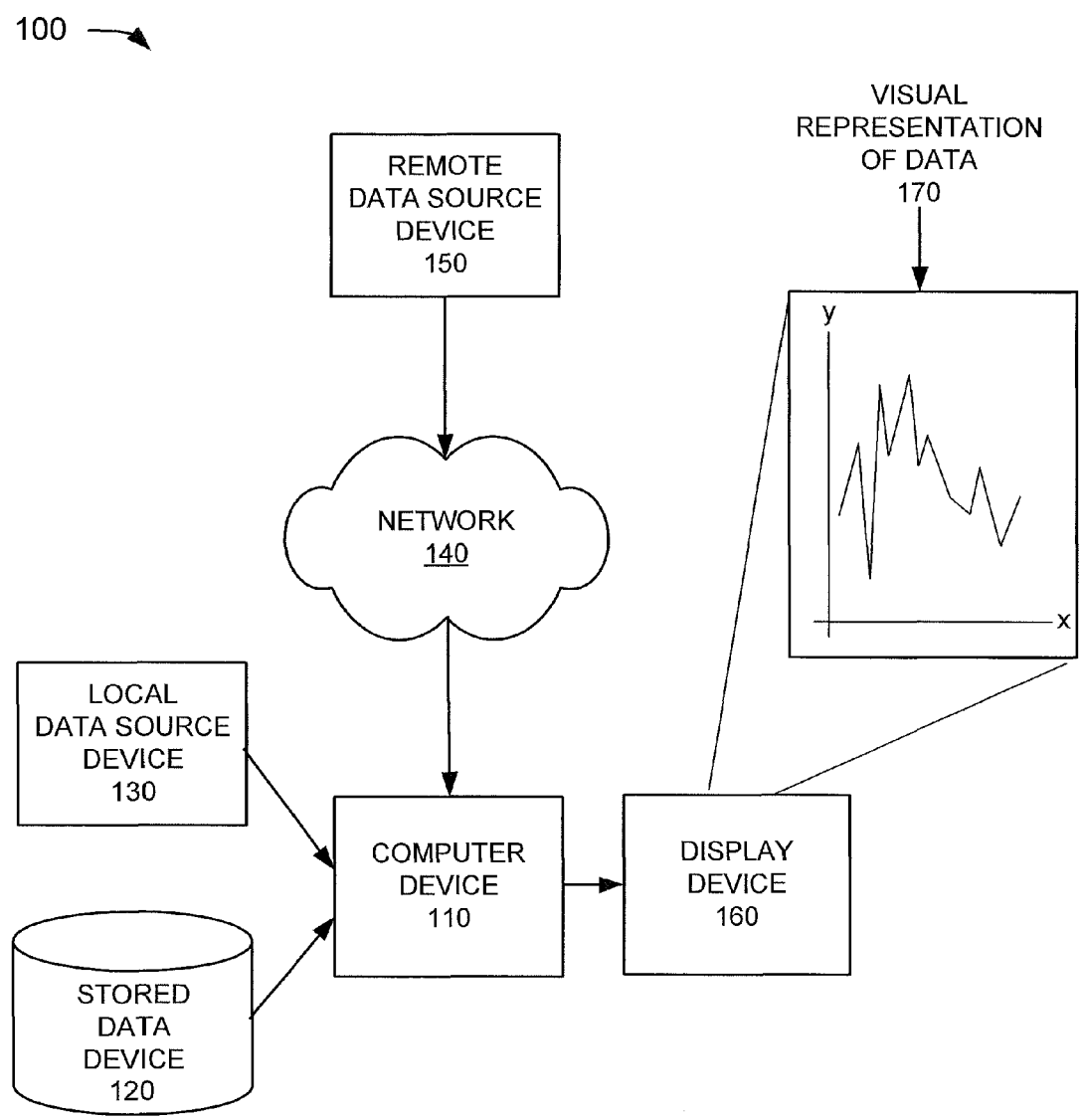
FIG. 1 is a diagram illustrating an example of components of a system according to an implementation described herein.

FIG. 1 is a diagram of an example system 100 according to an implementation described herein. As shown in FIG. 1, system 100 may include a computer device 110, a stored data device 120, a local data source device 130, a network 140, a remote data source device 150, and a display device 160.

Computer device 110 may include a computation device, such as a personal computer, a wireless telephone, a personal digital assistant (PDA), a laptop, a tablet, or another type of computation or communication device. In one implementation, computer device 110 may include a graphical modeling application.

Stored data device 120 may include a device that may act as a source of locally stored data with respect to computer device 110. For example, stored data device 120 may include a persistent storage device (e.g., a non-transitory computer-readable medium), such as a floppy disk device, a hard disk device, an optical disk device, a tape device, a flash memory or other similar solid state memory device, or an array of devices, including devices in a storage area network or other configurations.

Local data source device 130 may include a device that may act as a source of locally streamed data (e.g., data provided in real time) to computer device 110. For example, local data source device 130 may include a sensor, a data receiver device (e.g., a wireless receiver), an input device, and/or another computer device analogous to computer device 110.

Network 140 may include a network for exchanging information between devices connected to the network. For example, network 140 may exchange data, messages, etc. between remote data source device 150 and computer device 110. Embodiments of network 140 may include circuit-switched network and/or a packet-switched network, such as, for example, a local area network (LAN), a wide area network (WAN), a metropolitan area network (MAN), an optical network, a cable television network, a satellite television network, a wireless network (e.g., a Code Division Multiple Access (CDMA) network, a general packet radio service (GPRS) network, and/or a Long Term Evolution (LTE) network), an ad hoc network, a telephone network (e.g., the Public Switched Telephone Network (PSTN) or a cellular network), an intranet, the Internet, or a combination of networks.

Remote data source device 150 may include a device that may act as a remote data source to computer device 110, providing either stored or streaming data to computer device 110 across network 140. For example, remote data source device 150 may include a remote device analogous to stored data device 120 and/or local data source device 130.

Display device 160 may display data in association with computer device 110. For example, computer device 110 may receive data from stored data device 120, local data source device 130, and/or remote data source device 150. Computer device 110 may determine a data type for the received data, may generate a visual representation of the data based on the determined data type, and may forward the visual representation of the received data to display device 160. Display device 160 may display a visual representation 170 of the data. Display device 160 may include, for example, a TFT LCD (Thin-Film-Transistor Liquid Crystal Display), an OLED (Organic Light Emitting Diode) display, a cathode ray tube device, and/or any other appropriate display technology.

Although FIG. 1 shows example components of system 100, in other implementations, system 100 may include fewer components, different components, differently arranged components, and/or additional components than those depicted in FIG. 1. Alternatively, or additionally, one or more components of system 100 may perform one or more tasks described as being performed by one or more other components of system 100.

Figure 2:
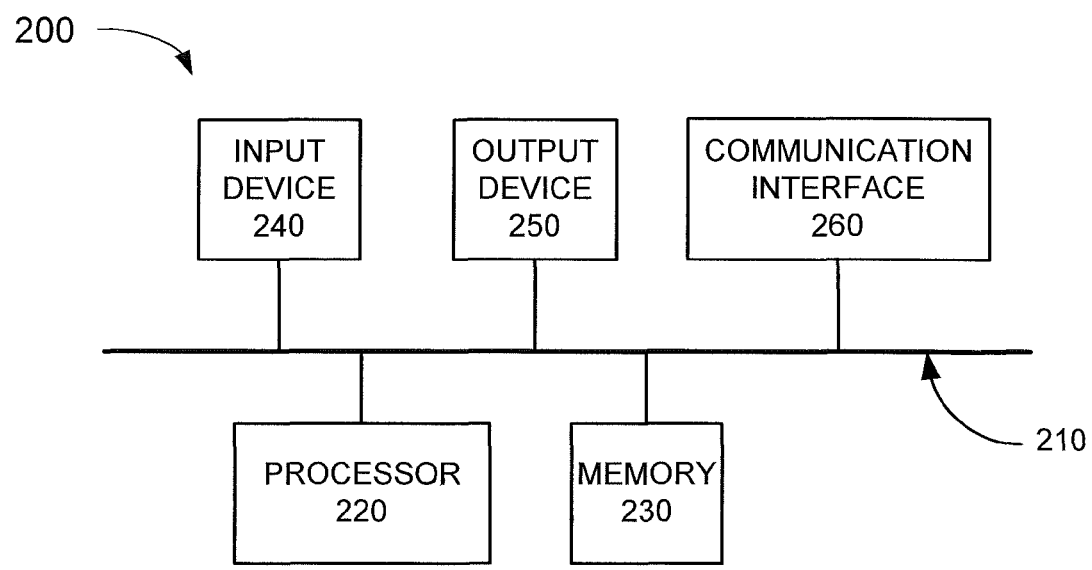
FIG. 2 is a diagram illustrating example components of a computer device according to an implementation described herein.

FIG. 2 is a diagram illustrating example components of computer device 110 according to a first implementation described herein. As shown in FIG. 2, computer device 110 may include a bus 210, a processor 220, a memory 230, an input device 240, an output device 250, and a communication interface 260.

Bus 210 may include a path that permits communication among the components of computer device 110. Processor 220 may include one or more processors, microprocessors, or processing logic (e.g., application specific integrated circuits (ASICs) or field programmable gate arrays (FPGAs)) that may interpret and execute instructions. Memory 230 may include a RAM device or another type of dynamic storage device that may store information and instructions for execution by processor 220, a ROM device or another type of static storage device that may store static information and instructions for use by processor 220, a magnetic and/or optical recording memory device and its corresponding drive, and/or a removable form of memory, such as a flash memory.

Input device 240 may include a mechanism that permits an operator to input information to computer device 110, such as a keypad, a keyboard, a button, or an input jack for an input device such as a keypad or a keyboard, etc. Output device 250 may include a mechanism that outputs information to the operator, including one or more light indicators, a display, a speaker, etc. In one example, output device 250 may include display device 160. In another example, output device 250 may be separate from, and possibly remote from, display device 160.

Communication interface 260 may include any transceiver-like mechanism that enables computer device 110 to communicate with other devices and/or systems. For example, communication interface 260 may include a modem, a network interface card, and/or a wireless interface card.

As will be described in detail below, computer device 110 may perform certain operations. Computer device 110 may perform these operations in response to processor 220 executing software instructions stored in a computer-readable medium, such as memory 230.

The software instructions may be read into memory 230 from another computer-readable medium, or from another device via communication interface 260. The software instructions contained in memory 230 may cause processor 220 to perform processes that will be described later. Alternatively, hardwired circuitry may be used in place of or in combination with software instructions to implement processes described herein. Thus, implementations described herein are not limited to any specific combination of hardware circuitry and software.

Although FIG. 2 shows example components of computer device 110, in other implementations, computer device 110 may include fewer components, different components, additional components, or differently arranged components than depicted in FIG. 2. Additionally or alternatively, one or more components of computer device 110 may perform one or more tasks described as being performed by one or more other components of computer device 110.

FIG. 3 is a diagram of example functional components of computer device 110 according to an implementation described herein. As shown in FIG. 3, computer device 110 may include a data analyzer 310, a data patterns database 320, a visual adapter selector 330, a visual adapter database 335, one or more visual adapters 340-A to 340-N (referred to herein collectively as "visual adapters 340" and individually as "visual adapter 340"), and a display component 350.

Data analyzer 310 may receive incoming data 301 and may analyze the incoming data for a pattern. Data analyzer 310 may initially attempt to select a data type for incoming data 301 based on a file extension and/or based on a file header associated with incoming data 301. For example, data analyzer 310 may attempt to compare a file extension, associated with incoming data 301, to a data store (e.g., a list) of file extensions and/or may compare a file header, associated with incoming data 301, with a data store (e.g., a stored list) of file headers. If data analyzer 310 cannot identify a data type based on a file extension and/or a file header, data analyzer 310 may select a data type for incoming data 301 based on a data sample.

For example, data analyzer 310 may extract a data sample from the incoming data and may compare the data sample to data patterns stored in data patterns database 320. If data analyzer 310 identifies the data sample as corresponding to a data pattern stored in data patterns database 320, data analyzer 310 may select a data type for the incoming data based on the identified data pattern. Data analyzer 310 may forward the selected data type to visual adapter selector 330.

If data analyzer 310 does not identify the data sample as corresponding to any data patterns stored in data patterns database 320, data analyzer 310 may output an indication that no data type was selected and may prompt a user to manually select a data type. Data patterns database 320 may include a non-transitory computer-readable medium that stores information relating data patterns to data types. Example fields stored in data patterns database 320 are described below with reference to FIG. 4A.

Visual adapter selector 330 may select a particular visual adapter for incoming data 301 based on the selected data type received from data analyzer 310 and by accessing visual adapter database 335. If visual adapter selector 330 identifies a particular visual adapter for incoming data 301 based on the selected data type, visual adapter selector 330 may select the particular visual adapter and may activate the particular visual adapter to generate a visual representation of incoming data 301. Visual adapter database 335 may include a non-transitory computer-readable medium that stores information relating data types to visual adapters. Example fields stored in visual adapter database 335 are described below with reference to FIG. 4B.

Visual adapter 340 may generate a visual representation for a particular data type. For example, visual adapter 340-A may generate a one dimensional graph based on incoming data 301, visual adapter 340-B may generate a two dimensional graph based on incoming data 301, visual adapter 340-C may generate a three dimensional graph based on incoming data 301, visual adapter 340-D may generate a video stream based on incoming data 301, visual adapter 340-E may generate a visual representation of an audio stream based on incoming data 301, visual adapter 340-F may generate a diagnostics window based on incoming data 301, etc.

Display component 350 may display the visual representation of incoming data 301 generated by visual adapter 340. In one example, display component 350 may include a graphical element (e.g., a display window) in a window of a modeling application (e.g., MATLAB® and/or Simulink®). In another example, display component 350 need not be associated with a modeling application.

Although FIG. 3 shows example functional components of computer device 110, in other implementations, computer device 110 may include fewer functional components, different functional components, differently arranged functional components, or additional functional components than depicted in FIG. 3. Additionally or alternatively, one or more functional components of computer device 110 may perform one or more tasks described as being performed by one or more other functional components of computer device 110.

FIG. 4A is a diagram of example fields that may be stored in data patterns database 320 according to an implementation described herein. In one implementation, data patterns database 320 may be implemented in a storage device included as part of memory 220. In another implementation, data patterns database 320 may be stored in a memory associated with another device or a group of devices, separate from or including memory 220.

As shown in FIG. 4A, data patterns database 320 may include data pattern entries 410 (referred to herein collectively as "data pattern entries 410" and individually as "data pattern entry 410") and corresponding data type entries 420 (referred to herein collectively "data type entries 420" and individually as "data type entry 420").

Data pattern entry 410 may include information about a particular data pattern. Data type entry 420 may specify a particular data type associated with a corresponding data pattern entry 410. In one example, data pattern entry 410 may include a pattern of data, such as a sequence of bits associated with a particular frame header. In another example, data pattern entry 410 may include one or more attributes that describe a particular data pattern. For example, data pattern entry 410 may include information about a dimensionality of data (e.g., how many values are included in each coupling of data).

Data pattern entry 410 may further include information about whether a particular dimension of data is associated with a particular range. Data pattern entry 410 may further include information about whether the data is associated with repeating frames and may further include a size range associated with the repeating frames (e.g., a range of sample values per frame). For example, video frames may be associated with larger number of sample values than audio frames. Data pattern entry 410 may further include information about whether the data includes particular control bits.

For example, for a data pattern entry 410 corresponding to a video data type, data pattern entry 410 may include the following information:
1) Dimensions: 3
2) Range of data in each dimension: 0 to 255
3) Repeating Frames: yes As another example, a data pattern entry 410 corresponding to a diagnostics data type may store a particular bit pattern, which, when detected as being repeated in a data sample, may be indicative of control bits or signal frames associated with data being provided by a diagnostics device.

Although FIG. 4A shows example fields that may be stored in data patterns database 320, in other implementations, data patterns database 320 may include fewer fields, different fields, differently arranged fields, and/or additional fields than depicted in FIG. 4A.

FIG. 4B is a diagram of example fields that may be stored in visual adapter database 335 according to an implementation described herein. In one implementation visual adapter database 335 may be implemented in a storage device included as part of memory 220. In another implementation, visual adapter database 335 may be stored in a memory associated with another device or a group of devices, separate from or including memory 220.

As shown in FIG. 4B, visual adapter database 335 may include data type entries 420 and corresponding visual adapter entries 430 (referred to herein collectively "visual adapter entries 430" and individually as "visual adapter entry 430").

Data type entries 420 may correspond to entries included in data patterns database 320. Visual adapter entries 430 may associate particular visual adapters with particular data type entries 420. For example, a three dimensional data type may be associated with a visual adapter that generates a three dimensional graph.

Although FIG. 4B shows example fields that may be stored in visual adapter database 335, in other implementations, visual adapter database 335 may include fewer fields, different fields, differently arranged fields, and/or additional fields than depicted in FIG. 4B.

Figure 5:
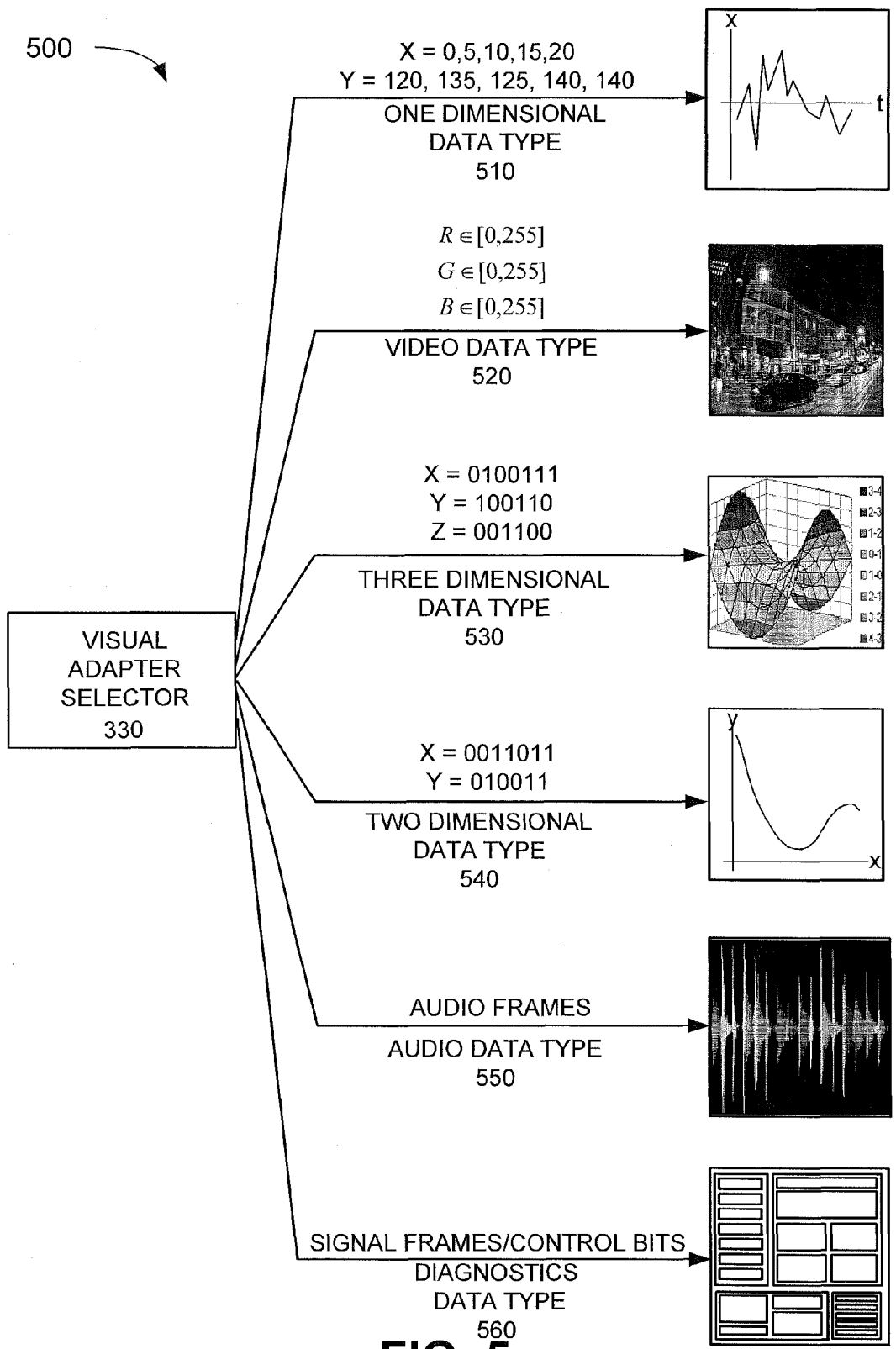
FIG. 5 is a diagram of example data patterns and associated data types according to an implementation described herein.

FIG. 5 is a diagram of example data patterns 500 and associated data types according to an implementation described herein. As shown in FIG. 5, example data patterns 500 may include a one dimensional data type 510, a video data type 520, a three dimensional data type 530, a two dimensional data type 540, an audio data type 550, and a diagnostics data type 560. In the examples described below, the particular delimiters of data shown (e.g., commas, parentheses, spaces, etc.) are examples only and any delimiters may be used and recognized by data analyzer 310. Furthermore, while the examples are given using decimal values, any other format and/or number base may be used (e.g., hexadecimal, binary, ASCII, etc.).

One dimensional data type 510 may include data that chronicles one or more variables with respect to an increasing variable (e.g., with respect to time, distance, etc.). An example of one dimensional data type 510 may include the following data:

(0, 120) (5, 135) (10, 125), (15, 140), (20, 140), . . . .

As this example shows, one dimensional data type 510 includes couplings of data, where in each coupling, one variable increases at a linear rate. One dimensional data type 510 may be associated with a visual adapter that generates a one dimensional graph.

Video data type 520 may include video data. Video data may include data organized in three dimensions and including a range associated with a color scheme (e.g., a Red Green Blue (RGB) color scheme). An example of video data type 520 may include data of the following format:

(255, 153, 153), (255, 153, 153), (255, 0, 153), (204, 204, 204), (204, 255, 51), . . . .

As this example shows, video data type 520 may include couplings of data, where each coupling includes three values in a range from 0 to 255. Video data type 520 may include with values associated with another type of color scheme, such as a Hue Saturation Lightness (HSV), Hue Saturation Value (HSV), Cyan Magenta Yellow Key (CMYK), etc. In some color schemes (e.g., CMYK), a different number of dimensions may be used (e.g., data couplets with four values).

Video data type 520 may include other data patterns that may be used by data analyzer 310 to detect video data type 520. For example, video data type 520 may include video frames, where each video frame includes a header. A header may include a synchronization word (syncword or preamble) that may be repeated in the header of each frame. In one example, data analyzer 310 may detect video data type 520 by detecting video frames (e.g., by detecting a repeating syncword). In another example, data analyzer 310 may detect video data type 520 by detecting video frames in combination with detecting data organized in three dimensions and including a range associated with a color scheme. Video data type 520 may be associated with a visual adapter that displays a video stream based on the video data.

Three dimensional data type 530 may include data in three dimensions. An example of three dimensional data type 530 may include the following data:

(23, 0.022, 543000), (30, 0.054, 543000), (45, 0.025, 504000), (50, 0.030, 475000), . . . .

As this example shows, three dimensional data type 530 may include couplings of data, where each coupling includes three values. Three dimensional data type 530 may be associated with a visual adapter that generates a three dimensional graph.

Two dimensional data type 540 may include data in two dimensions. An example of two dimensional data type 540 may include the following data:

(65, 90), (67, 92), (70, 85), (68, 88), (67, 85), . . . .

As this example shows, two dimensional data type 540 includes couplings of data, where each coupling includes two values. Two dimensional data type 540 may be associated with a visual adapter that generates a two dimensional graph.

Audio data type 550 may include audio frames, where each audio frame includes a header. A header may include a synchronization word (syncword or preamble) that may be repeated in the header of each frame. Data analyzer 310 may detect audio data type 550 by detecting audio frames (e.g., by detecting a repeating syncword). Audio data type 550 may be associated with a visual adapter that displays a visual representation of an audio stream based on the audio data. The visual representation of the audio stream may correspond to, for example, a spectral graph of the audio stream.

While video data type 520 and audio data type 550 may both include frames, data analyzer 310 may distinguish audio data type 520 from video data type 550 using various distinguishing features. For example, audio frames may be associated with a first size range and video frames may be associated with a second size range, where the second size range is larger than the first size range. Furthermore, video frames may be associated with data in three dimensions with data values within the range of a color scheme, while audio frames may not be associated with data in three dimensions or with data values within a particular range.

Diagnostics data type 560 may include control bits and/or signal frames associated with data from a diagnostics computer (e.g., a vehicle engine computer). An example of diagnostics data type 560 may include the following data:

(signal frame, s_coolant, 220, s_oxygen, 0.5, s_mp, 50, . . .

where "signal frame" may correspond to a sequence of bits that indicates the beginning of a signal frame, "s_coolant" may correspond to a sequence of bits identifying data associated with a coolant sensor, "s_oxygen" may correspond to a sequence of bits identifying data associated with an oxygen sensor, "s_mp" may correspond to a sequence of bits identifying data associated with a manifold pressure sensor, etc. Diagnostics data type 560 may be associated with a visual adapter that generates a diagnostics window based on diagnostics data. For example, the diagnostics window may include a group of boxes each displaying a value of a sensor associated with a device that is streaming the diagnostics data to computer device 110. Thus, the diagnostics window may include a box that displays a coolant temperature value, a box that displays an amount of unburnt oxygen, a box that displays a manifold absolute pressure, etc.

Figure 6:
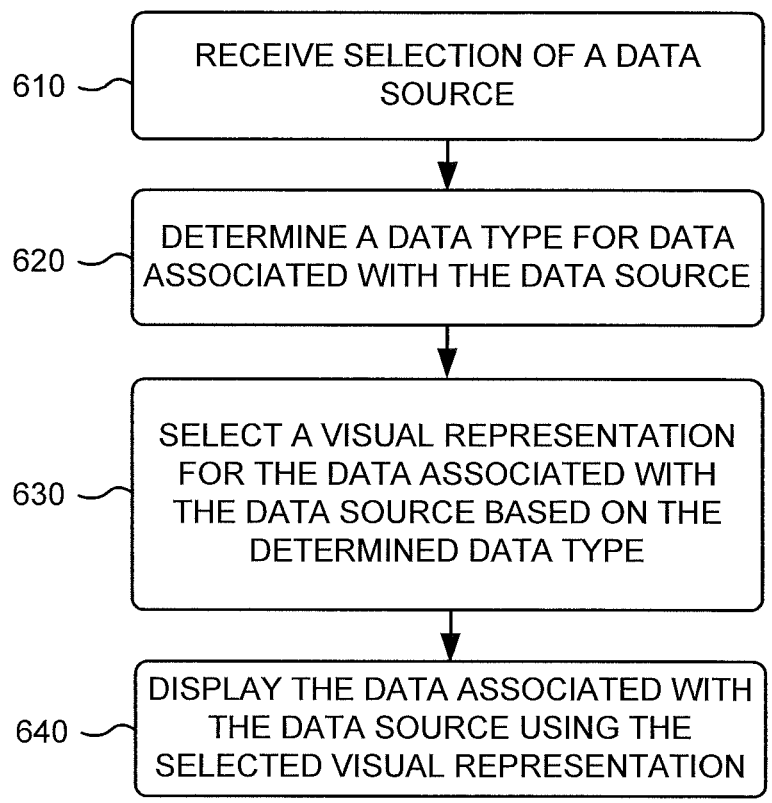
FIG. 6 is flow diagram illustrating a process for selecting a visual representation for a data type according to an implementation described herein.

FIG. 6 is flow diagram illustrating a process for selecting a visual representation for a data type according to an implementation described herein. In one implementation, the process of FIG. 6 may be performed by computer device 110. In other implementations, some or all of the process of FIG. 6 may be performed by another device or a group of devices separate from and/or possibly remote from computer device 110 and/or including computer device 110.

The process of FIG. 6 may include receiving a selection of a data source (block 610). A user may specify a particular source of data by selecting to open a file or by selecting a source of streaming data. The user may create a graphical element in a graphical modeling environment and may link the graphical element to a data source. For example, the user may request a file from stored data device 120, specify a port on computer device 110 associated with local data source device 130, and/or specify a network address, such as a uniform resource locator (URL) associated with remote data source device 150.

A data type for data associated with the data source may be determined (block 620). For example, data analyzer 310 may determine a data type based on a file extension or a file header included in data associated with the selected data source. If data analyzer 310 cannot determine a data type based on a file extension or a file header, data analyzer 310 may determine a data pattern associated with the selected data source. For example, data analyzer 310 may receive a data sample from the selected data source and may analyze the received data sample for a data pattern. A process for analyzing a data pattern is described below with reference to FIG. 7. Data analyzer 310 may select a particular data type based on a determined data pattern by accessing data patterns database 320.

A visual representation for the data, associated with the data source, may be selected based on the determined data type (block 630). For example, visual adapter selector 330 may select a visual adapter 340 associated with the determined data type by accessing visual adapter database 335. The visual adapter 340 may generate a particular visual representation of data received from the selected data source. For example, if the data type corresponds to a two dimensional data type, visual adapter 340 may generate a two dimensional graph based on data received from the selected data source.

The data, associated with the data source, may be displayed using the selected visual representation (block 640). For example, the user may link display component 350 in the graphical modeling environment to the selected data source and display component 350 may display the generated visual representation of the data associated with the selected data source. For example, if the data corresponds to a two dimensional data type, display component 350 may display the generated two dimensional graph. If the selected data source corresponds to a streaming data source, display component 350 may continue to update the displayed visual representation as data continues to be received from the selected data source. For example, display component 350 may continue to plot additional data on the displayed two dimensional graph as the data is being streamed from the selected data source.

Figure 7:
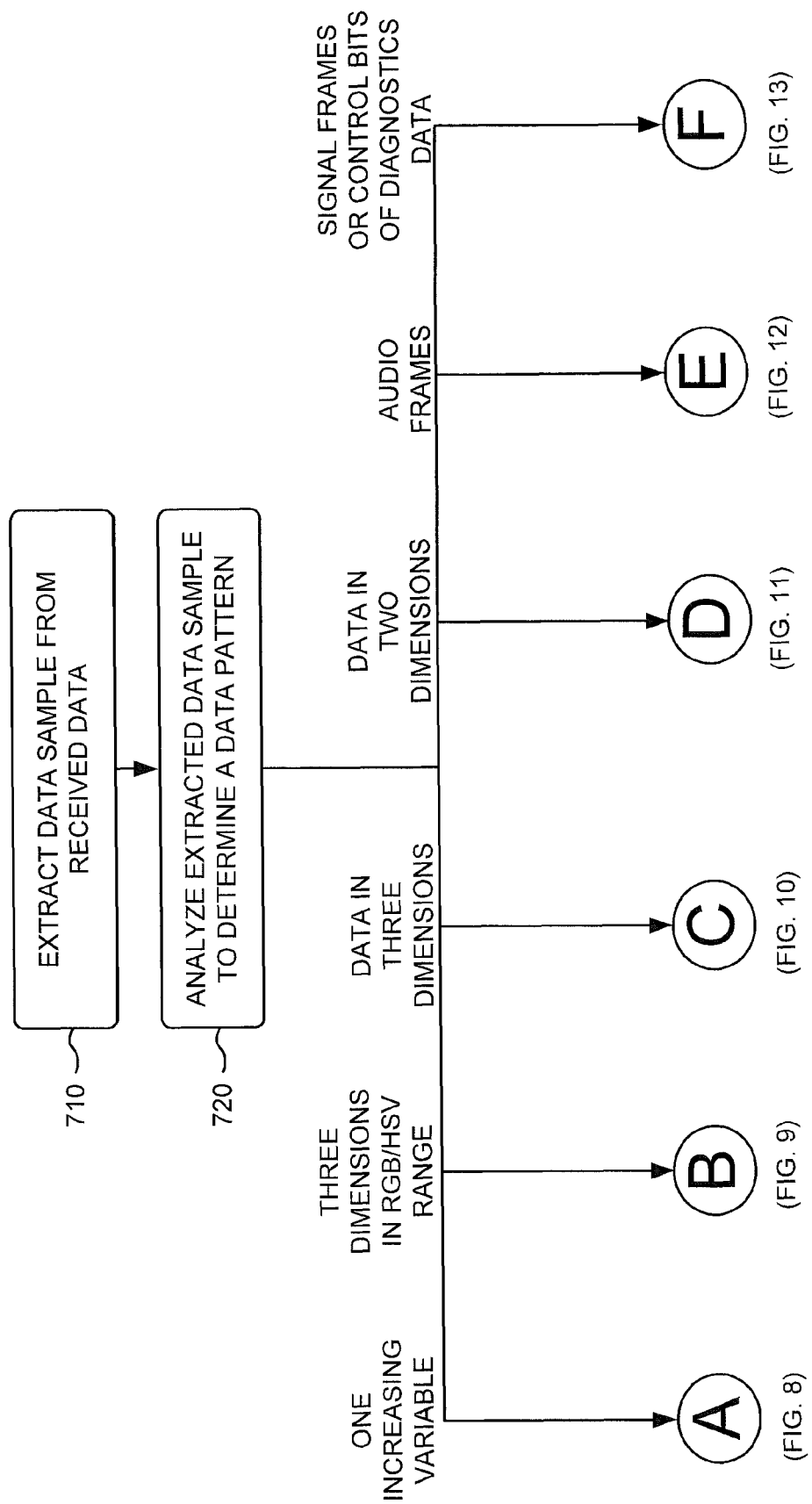
FIG. 7 is a flow diagram illustrating a process for analyzing a data pattern according to an implementation described herein.

FIG. 7 is a flow diagram illustrating a process for analyzing a data pattern according to an implementation described herein. In one implementation, the process of FIG. 7 may be performed by computer device 110. In other implementations, some or all of the process of FIG. 7 may be performed by another device or a group of devices separate from and/or possibly remote from computer device 110 and/or including computer device 110.

The process of FIG. 7 may include extracting a data sample from the received data (block 710). For example, data analyzer 310 may extract a sample of data from incoming data 301. The extracted data sample may be analyzed to determine a data pattern (block 720). For example, data analyzer 310 may determine whether a data pattern can be identified in the extracted data sample by accessing data patterns database 320. In one example, data analyzer 310 may determine a first delimiter that separates groups of individual data points and a second delimiter that separates individual data points. Based on the determined delimiters, data analyzer 310 may determine how data points are organized within the extracted data sample and may determine a dimension associated with the extracted data sample. In another example, data analyzer 310 may identify one or more characters and/or one or more patterns of bits that repeat at particular intervals or that are indicative of a frame header by accessing data patterns database 320.

Figure 8:
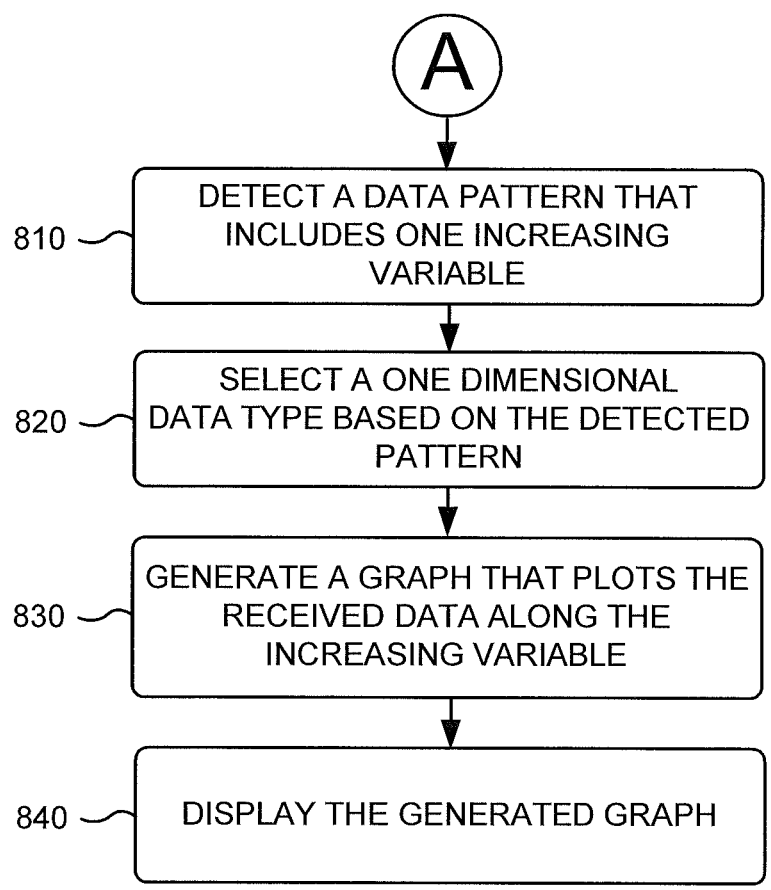
FIG. 8 is a flow diagram illustrating a process for displaying data associated with a one dimensional data type according to an implementation described herein.
Figure 9:
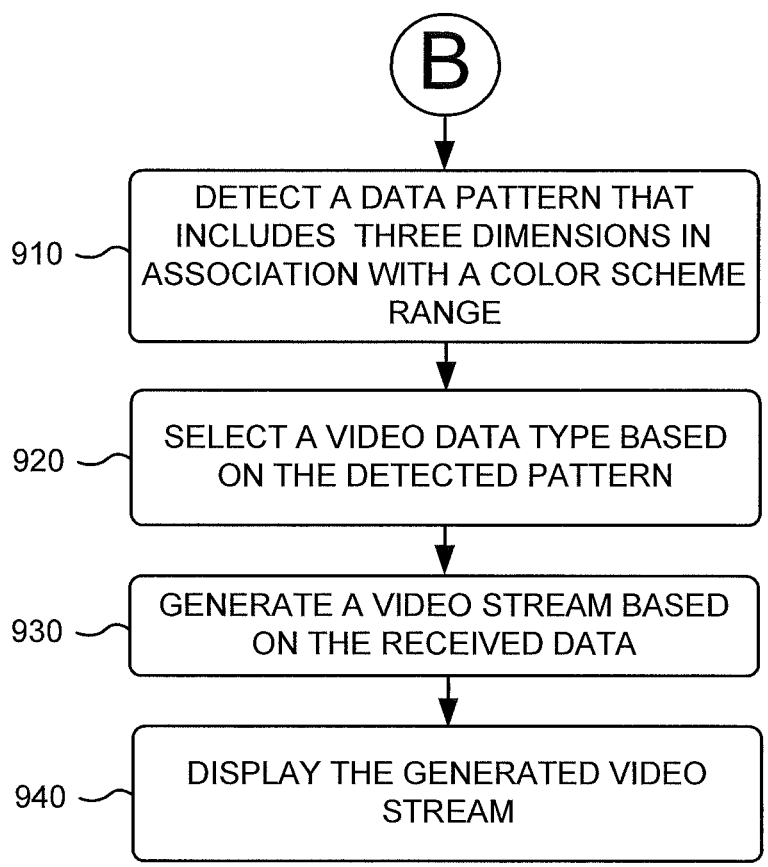
FIG. 9 is a flow diagram illustrating a process for displaying data associated with a video data type according to an implementation described herein.
Figure 10:
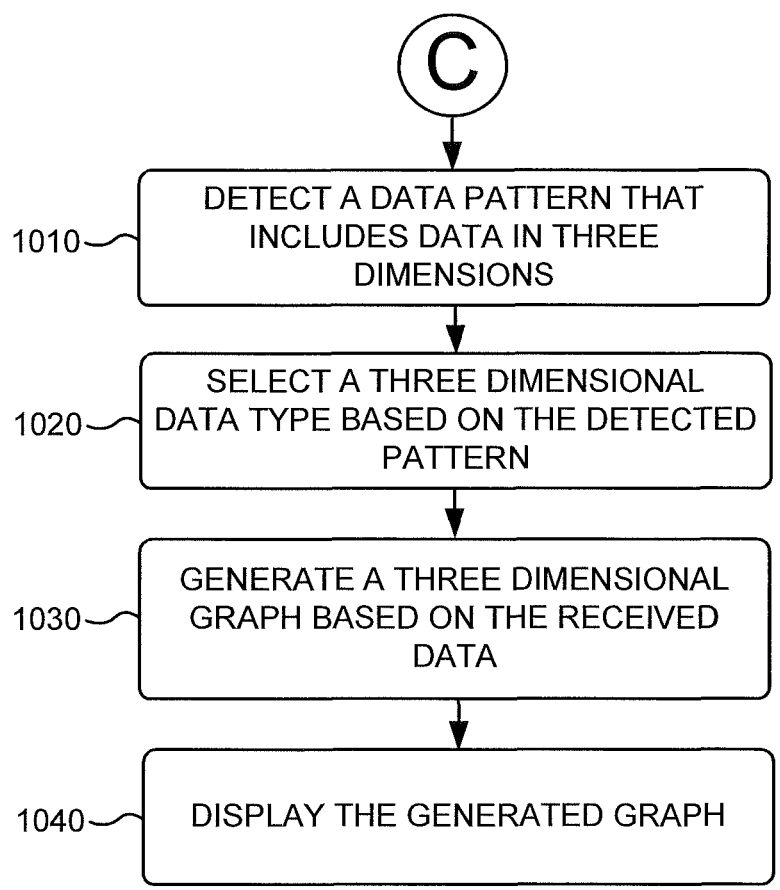
FIG. 10 is a flow diagram illustrating a process for displaying data associated with a three dimensional data type according to an implementation described herein.
Figure 11:
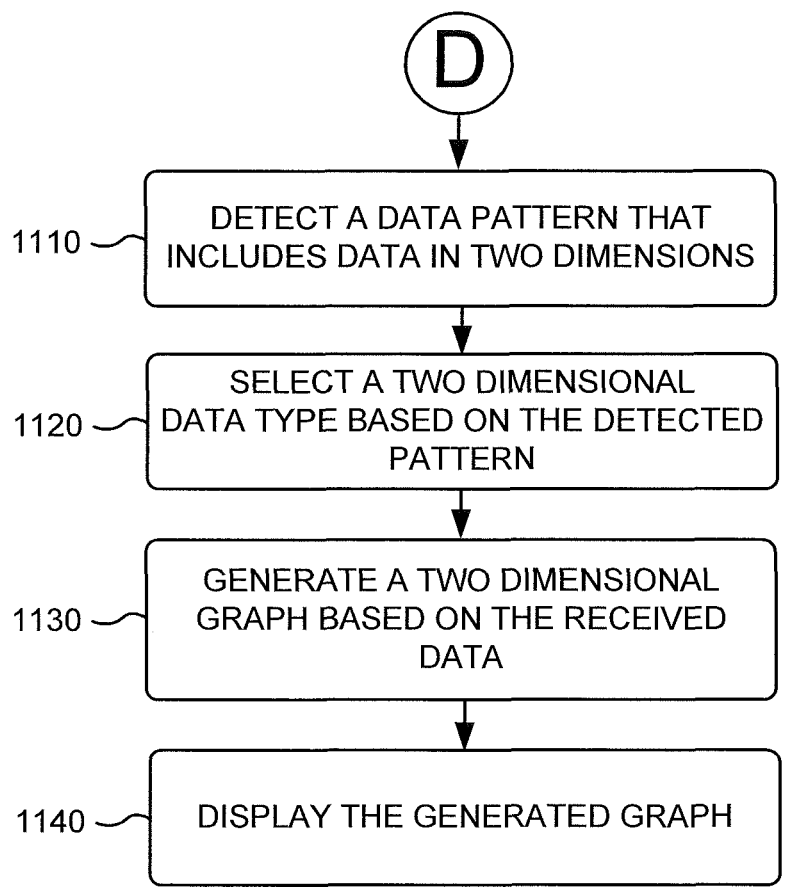
FIG. 11 is a flow diagram illustrating a process for displaying data associated with a two dimensional data type according to an implementation described herein.
Figure 12:
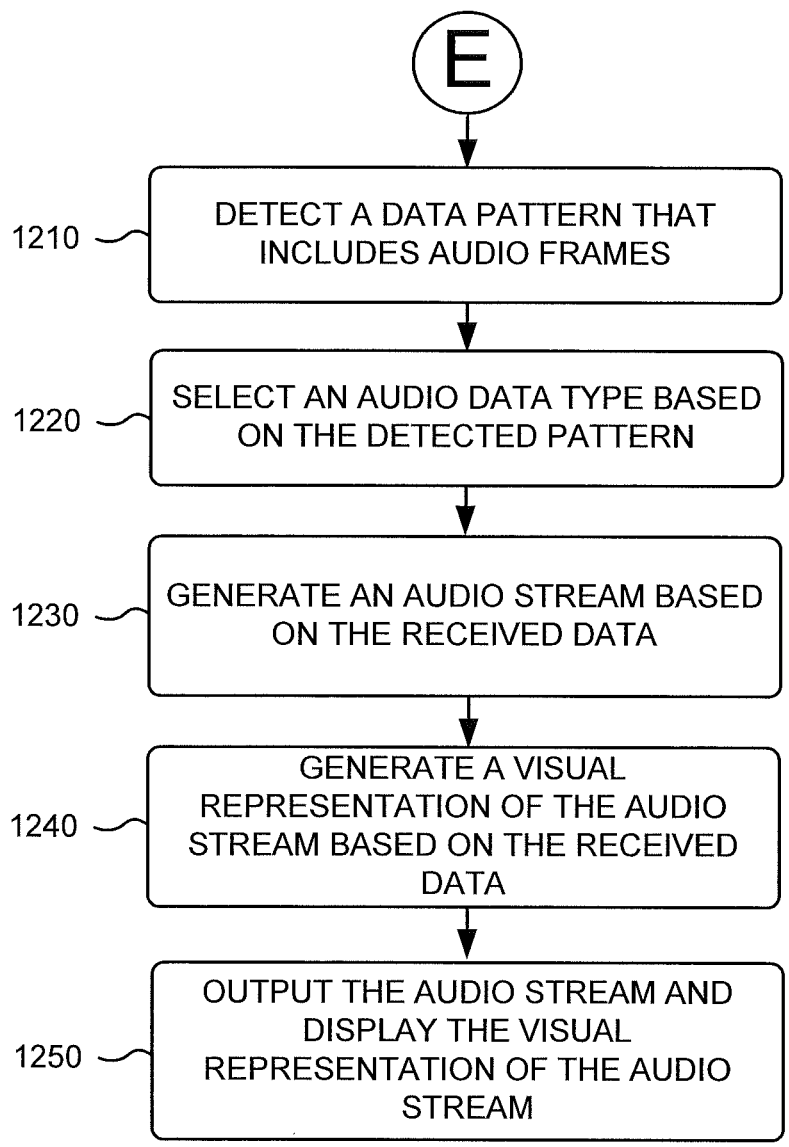
FIG. 12 is a flow diagram illustrating a process for displaying data associated with an audio data type according to an implementation described herein.
Figure 13:
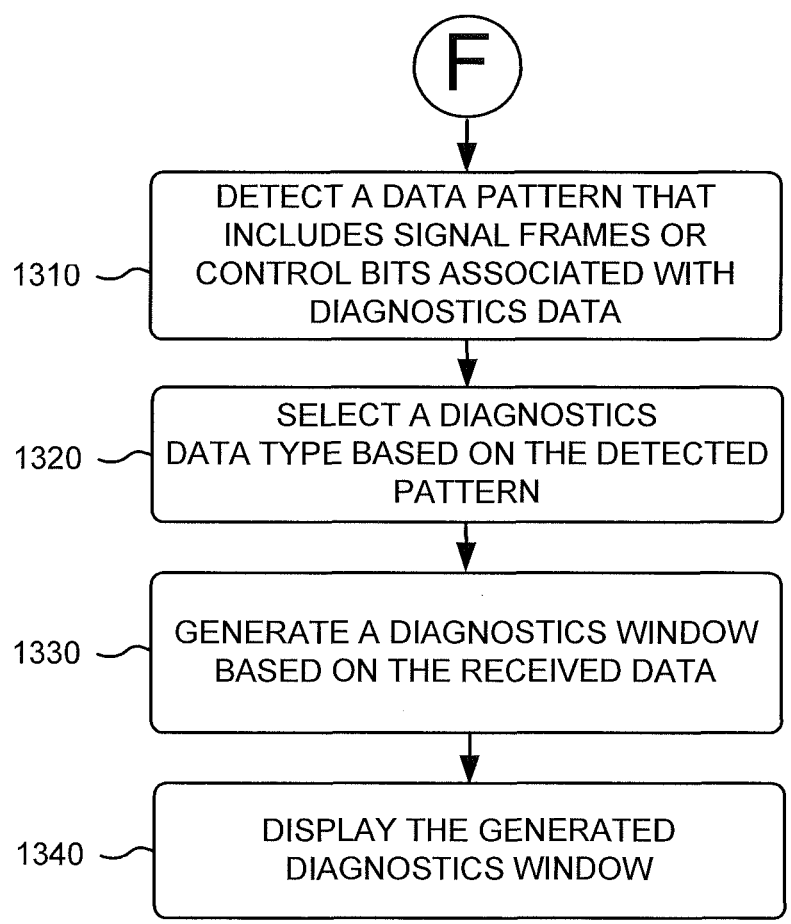
FIG. 13 is a flow diagram illustrating a process for displaying data associated with a diagnostics data type according to an implementation described herein.

If a data pattern associated with one increasing variable is determined, processing may proceed as shown in FIG. 8. If a data pattern associated with three dimensions and a color scheme range is determined, processing may proceed as shown in FIG. 9. If a data pattern associated with data in three dimensions is determined, processing may proceed as shown in FIG. 10. If a data pattern associated with data in two dimensions is determined, processing may proceed as shown in FIG. 11. If a data pattern associated with audio frames is determined, processing may proceed as shown in FIG. 12. If a data pattern associated with signal frames or control bits associated with diagnostics data is determined, processing may proceed as shown in FIG. 13.

FIG. 8 is a flow diagram illustrating a process for displaying data associated with a one dimensional data type according to an implementation described herein. In one implementation, the process of FIG. 8 may be performed by computer device 110. In other implementations, some or all of the process of FIG. 8 may be performed by another device or a group of devices separate from and/or possibly remote from computer device 110 and/or including computer device 110 (e.g., via a cloud computing environment).

The process of FIG. 8 may include detecting a data pattern that includes one increasing variable (block 810). For example, data analyzer 310 may determine that the extracted data sample includes couplings of data, where subsequent couplings of data include one variable that is increasing. For example, in a data sample that includes the following data: {(0, 120) (5, 135) (10, 125), (15, 140), (20, 140)}, the progression of the first variable from 0, to 5, to 10, to 15, to 20 may indicate an increasing variable.

A one dimensional data type may be selected based on the detected pattern (block 820). For example, data analyzer 310 may select a one dimensional data type for the received data based on data patterns database 320. A graph may be generated that plots the received data along the increasing variable (block 830). For example, visual adapter selector 330 may select a one dimensional visual adapter for the selected one dimensional data type based on visual adapter database 335, and the selected one dimensional visual adapter may generate a one dimensional graph, plotting one or more variables as functions of the increasing variable.

The generated graph may be displayed (block 840). For example, display component 350 may display the generated one dimensional graph. The one dimensional graph may continue to be updated as additional data is received from the selected data source (e.g., if the selected data source continues to stream data).

FIG. 9 is a flow diagram illustrating a process for displaying data associated with a video data type according to an implementation described herein. In one implementation, the process of FIG. 9 may be performed by computer device 110. In other implementations, some or all of the process of FIG. 9 may be performed by another device or a group of devices separate from and/or possibly remote from computer device 110 and/or including computer device 110.

The process of FIG. 9 may include detecting a data pattern that includes three dimensions in association with a color scheme range (block 910). For example, data analyzer 310 may determine that the extracted data sample includes couplings of data, where each coupling includes three values in the range of a color scheme (e.g., 0 to 255 for an RGB color scheme). For example, in a data sample that includes the following data: {(255, 153, 153), (255, 153, 153), (255, 0, 153), (204, 204, 204), (204, 255, 51)}, each coupling includes three values, where each value is in a range from 0 to 255. A video data type may be selected based on the detected pattern (block 920). For example, data analyzer 310 may select a video data type for the received data based on data patterns database 320.

Additional, or alternative, techniques may be used to select a video data type. For example, data analyzer 310 may determine whether the extracted data sample includes frame headers. In one example, data analyzer 310 may identify a particular bit pattern associated with a particular video format. In another example, data analyzer 310 may identify a bit pattern that repeats in the extracted data sample at a particular interval, where the particular interval is representative of a size of a video frame associated with a particular video format.

A video stream may be generated based on the received data (block 930). For example, visual adapter selector 330 may select a video visual adapter for the selected video data type based on visual adapter database 335, and the selected video visual adapter may generate a video stream based on the received data. The generated video stream may be displayed (block 940). For example, display component 350 may display the generated video stream.

FIG. 10 is a flow diagram illustrating a process for displaying data associated with a three dimensional data type according to an implementation described herein. In one implementation, the process of FIG. 10 may be performed by computer device 110. In other implementations, some or all of the process of FIG. 10 may be performed by another device or a group of devices separate from and/or possibly remote from computer device 110 and/or including computer device 110.

The process of FIG. 10 may include detecting a data pattern that includes data in three dimensions (block 1010). For example, data analyzer 310 may determine that the extracted data sample includes couplings of data, where each coupling of data includes three data values, and where the data is not associated with video frames and is not limited to a range of values associated with a color scheme. For example, in a data sample that includes the following data: {(23, 0.022, 543000), (30, 0.054, 543000), (45, 0.025, 504000), (50, 0.030, 475000)}, each coupling of data may include three data values.

A three dimensional data type may be selected based on the detected pattern (block 1020). For example, data analyzer 310 may select a three dimensional data type for the received data based on data patterns database 320. A three dimensional graph may be generated based on the received data (block 1030). For example, visual adapter selector 330 may select a three dimensional visual adapter for the selected three dimensional data type based on visual adapter database 335. The selected three dimensional visual adapter may generate a three dimensional graph that plots the second and third of the three variables as a function of the first variable.

The generated graph may be displayed (block 1040). For example, display component 350 may display the generated three dimensional graph. The three dimensional graph may continue to be updated as additional data is received from the selected data source (e.g., if the selected data source continues to stream data).

FIG. 11 is a flow diagram illustrating a process for displaying data associated with a two dimensional data type according to an implementation described herein. In one implementation, the process of FIG. 11 may be performed by computer device 110. In other implementations, some or all of the process of FIG. 11 may be performed by another device or a group of devices separate from and/or possibly remote from computer device 110 and/or including computer device 110.

The process of FIG. 11 may include detecting a data pattern that includes data in two dimensions (block 1110). For example, data analyzer 310 may determine that the extracted data sample includes couplings of data, where each coupling of data includes two data values. For example, in a data sample that includes the following data: {(65, 90), (67, 92), (70, 85), (68, 88), (67, 85)}, each coupling of data may include two data values.

A two dimensional data type may be selected based on the detected pattern (block 1120). For example, data analyzer 310 may select a two dimensional data type for the received data based on data patterns database 320. A two dimensional graph may be generated based on the received data (block 1130). For example, visual adapter selector 330 may select a two dimensional visual adapter for the selected two dimensional data type based on visual adapter database 335, and the selected two dimensional visual adapter may generate a two dimensional graph that plots the second of the two variables as a function of the first variable.

The generated graph may be displayed (block 1140). For example, display component 350 may display the generated two dimensional graph. The two dimensional graph may continue to be updated as additional data is received from the selected data source (e.g., if the selected data source continues to stream data).

FIG. 12 is a flow diagram illustrating a process for displaying data associated with an audio data type according to an implementation described herein. In one implementation, the process of FIG. 12 may be performed by computer device 110. In other implementations, some or all of the process of FIG. 12 may be performed by another device or a group of devices separate from and/or possibly remote from computer device 110 and/or including computer device 110.

The process of FIG. 12 may include detecting a data pattern that includes audio frames (block 1210). For example, data analyzer 310 may determine whether the extracted data sample includes frame headers. In one example, data analyzer 310 may identify a particular bit pattern associated with a particular audio format. In another example, data analyzer 310 may identify a bit pattern that repeats in the extracted data sample at a particular interval, where the particular interval is representative of a size of an audio frame associated with a particular audio format. An audio data type may be selected based on the detected pattern (block 1220). For example, data analyzer 310 may select an audio data type for the received data based on data patterns database 320.

An audio data stream may be generated based on the received data (block 1230). For example, visual adapter selector 330 may select an audio visual adapter for the selected audio data type based on visual adapter database 335, and the selected audio visual adapter may generate an audio stream based on the received data. A visual representation of the audio stream may be generated based on the received data (block 1240). For example, the selected audio visual adapter may generate a visual representation of the audio stream by, for example, plotting an amplitude of the audio signal as a function of time.

The generated audio stream may be output and the visual representation of the audio stream may be displayed (block 1250). For example, display component 350 may display the visual representation of the audio stream and the audio stream may be outputted via speakers associated with computer device 110.

FIG. 13 is a flow diagram illustrating a process for displaying data associated with a diagnostics data type according to an implementation described herein. In one implementation, the process of FIG. 13 may be performed by computer device 110. In other implementations, some or all of the process of FIG. 13 may be performed by another device or a group of devices separate from and/or possibly remote from computer device 110 and/or including computer device 110.

The process of FIG. 13 may include detecting a data pattern that includes signal frames and/or control bits associated with diagnostics data (block 1310). For example, data analyzer 310 may determine that the extracted data sample includes control bits and/or signal headers associated with diagnostics data. The a data sample may include the following data: {signal frame, s_coolant, 220, s_oxygen, 0.5, s_mp, 50}, "signal frame" may correspond to a sequence of bits that indicates the beginning of a signal frame, "s_coolant" may correspond to a sequence of control bits identifying data associated with a coolant sensor, "s_oxygen" may corresponds to a sequence of control bits identifying data associated with an oxygen sensor, and "s_mp" may corresponds to a sequence of control bits identifying data associated with a manifold pressure sensor. Thus, based on the presence of the "signal frame" bits, data analyzer 310 may determine that the received data corresponds to a diagnostics data type.

A diagnostics data type may be selected based on the detected pattern (block 1320). For example, data analyzer 310 may select a diagnostics data type for the received data based on data patterns database 320.

A diagnostics window may be generated based on the received data (block 1330). For example, visual adapter selector 330 may select a diagnostics visual adapter for the selected diagnostics data type based on visual adapter database 335, and the selected diagnostics visual adapter may generate a diagnostics window based on diagnostics data. The diagnostics window may include a group of boxes each displaying a value of a sensor associated with a device that is streaming the diagnostics data to computer device 110. Thus, the diagnostics window may include a box that displays a coolant temperature value, a box that displays an amount of unburnt oxygen, a box that displays a manifold absolute pressure, etc.

The generated diagnostics window may be displayed (block 1340). For example, display component 350 may display the generated diagnostics window. The diagnostics window may continue to be updated as additional data is received from the selected data source (e.g., if the selected data source continues to stream data).

While FIG. 5 illustrates examples of data types that may be automatically recognized and FIGS. 8-13 illustrate example processes for recognizing, selecting, and displaying particular data types, computer device 110 may recognize, select, and/or display fewer data types, different data types, differently arranged data types, and/or additional data types.

In one example, functionality for automatically handling additional data types may be manually added. For example, a user may designate a particular data source (e.g., a file or streaming data) as being of a particular data type and may add an entry into data patterns database 320 that includes a particular data pattern, associated with the particular data source, and a corresponding data type. Furthermore, the user may select a visual representation for the data type by adding an entry into visual adapter database 335.

In another example, computer device 110 may add entries to data patterns database 320 and to visual adapter database 335 without user input. For example, data analyzer 310 may detect a new data pattern and may create a new entry in data patterns database 320. Visual adapter selector 330 may scan data sources (e.g., stored data device 120, local data source device 130, and/or remote data source device 150) for information about the new data pattern. For example, visual adapter selector 330 may identify information indicative of a particular visual adapter in association with the new data pattern and may create a new entry in visual adapter database 335 based on the identified information.

Figure 14:
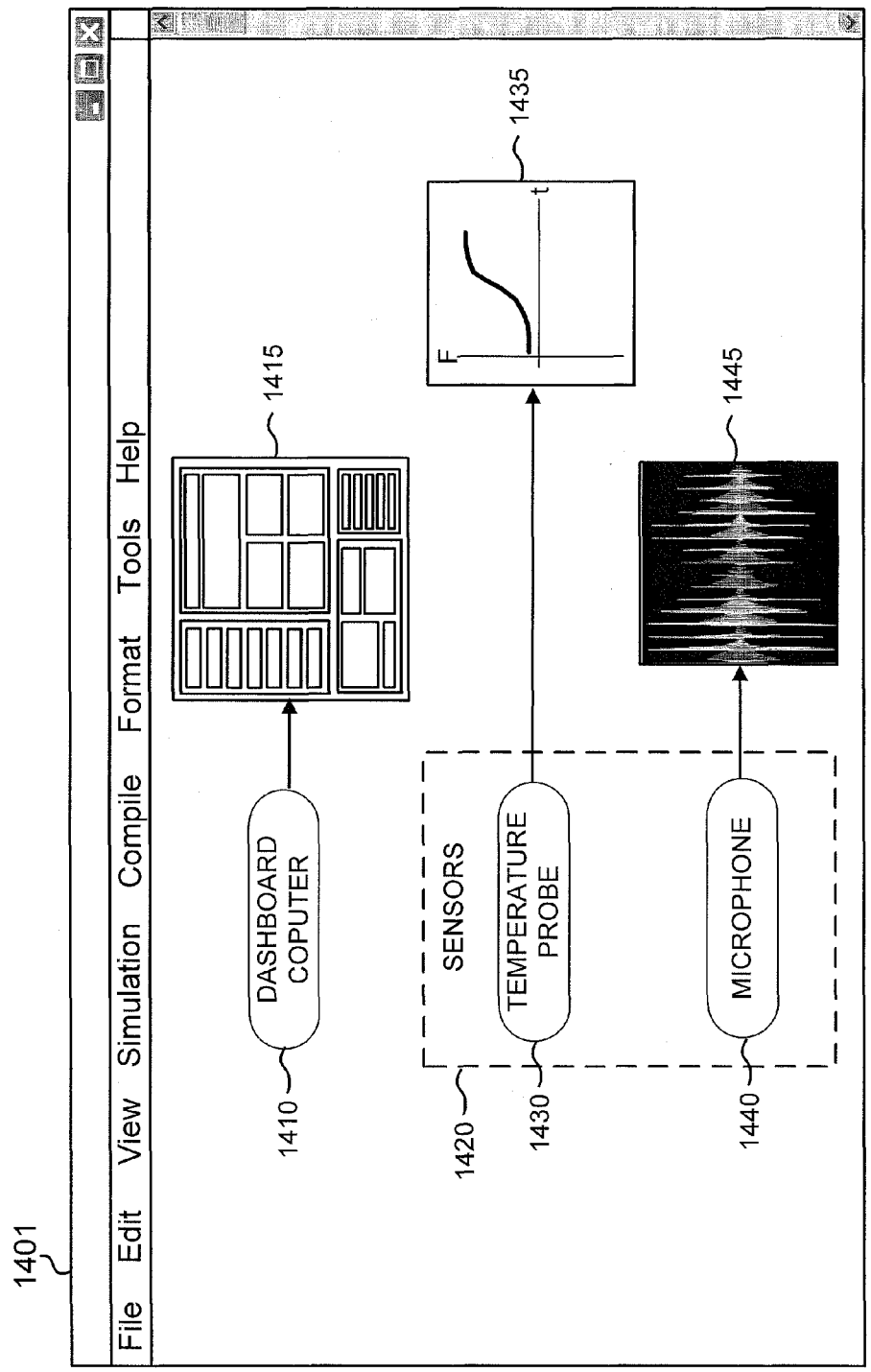
FIG. 14 is a diagram of an example user interface according to an implementation described herein.

FIG. 14 is a diagram of an example user interface 1401 according to an implementation described herein. Assume a user wishes to diagnose a car engine. The user may connect a dashboard computer connected to the car engine to port 1 of computer device 110. Furthermore, assume the user wishes to diagnose the car engine using additional sensors. The user may place a temperature probe at a particular location on the car engine and may connect the temperature probe to port 2 of computer device 110. Additionally the user may place a digital microphone at a particular location on the car engine and connect the digital microphone to port 3 of computer device 110.

The user may activate graphical modeling software (e.g., Simulink) and may create a first graphical element 1410, label first graphical element 1410 as "dashboard computer," and link the first graphical element 1410 to port 1. The user may create a first display component 1415 and may link first graphical element 1410 to first display component 1415. First graphical element 1410 may receive data from port 1. Data analyzer 310 may analyze the received data and may detect a diagnostics data type. Visual adapter selector 330 may select a diagnostics visual adapter to generate a diagnostics window, based on the detected diagnostics data type, and first display component 1415 may display the diagnostics window.

The user may create a second graphical element 1420 associated with sensors. The user may create a first sensor graphical element 1430 and may link first sensor graphical element 1430 to port 2. The user may create a second display element 1435 and may link first sensor graphical element 1430 to second display element 1435. Second graphical element 1430 may receive data from port 2. Data analyzer 310 may analyze the received data and may select a one dimensional data type. Visual adapter selector 330 may select a one dimensional visual adapter to generate a one dimensional graph, based on the detected one dimensional data type, and second display component 1435 may display the one dimensional graph.

The user may create a second sensor graphical element 1440 and may link second sensor graphical element 1440 to port 3. The user may create a third display element 1445 and may link second sensor graphical element 1440 to third display element 1445. Second sensor graphical element 1440 may receive data from port 3. Data analyzer 310 may analyze the received data and may select an audio data type. Visual adapter selector 330 may select an audio visual adapter to generate visual representation of an audio stream, based on the detected audio data type, and third display component 1445 may display the visual representation of the audio stream.

Thus, as shown in example user interface 1401, the user need not select or indicate a type of data or a type of display. Rather, the graphical modeling software may automatically display the appropriate data type for each data source.

The foregoing description of implementations, described above, provides illustration and description, but is not intended to be exhaustive or to limit the invention to the precise form disclosed. Modifications and variations are possible in light of the above teachings or may be acquired from practice of the invention.

While series of blocks have been described with regard to FIGS. 6-13, the order of the blocks may be modified in other implementations. Further, non-dependent blocks may be performed in parallel.

Also, certain portions of the implementations may have been described as a "component," "analyzer," "selector," or "adapter" that performs one or more functions. The terms "component," "analyzer," "selector," and "adapter" may include hardware, such as a processor, an ASIC, and/or a FPGA, or a combination of hardware and software (e.g., software running on a processor).

It will be apparent that aspects described herein may be implemented in many different forms of software, firmware, and hardware in the implementations illustrated in the figures. The actual software code or specialized control hardware used to implement aspects does not limit the embodiments. Thus, the operation and behavior of the aspects were described without reference to the specific software code—it being understood that software and control hardware can be designed to implement the aspects based on the description herein.

Even though particular combinations of features are recited in the claims and/or disclosed in the specification, these combinations are not intended to limit the disclosure of the invention. In fact, many of these features may be combined in ways not specifically recited in the claims and/or disclosed in the specification.

No element, act, or instruction used in the present application should be construed as critical or essential to the invention unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method comprising:
   receiving a graphical element, based on a user input and via a graphical modeling environment, for a streaming data source,
      the receiving being performed by a computer device;
   linking, based on the user input and via the graphical modeling environment, the graphical element to the streaming data source,
      the streaming data source providing data to the graphical element based on linking the streaming data source to the graphical element,
      the linking being performed by the computer device;
   linking the graphical element to a display component for displaying a visual representation of the data,
      the graphical element and the display component being provided for display via the graphical modeling environment,
      the linking the graphical element to the display component being performed by the computer device;
   determining a data type for the data,
      the determining the data type including:
         reading a portion of the data from the streaming data source,
            the read portion of the data including a coupling of data that includes at least two data points,
            the coupling of data representing data to be displayed within the visual representation of the data,
         analyzing the read portion of the data to determine a data pattern,
            the data pattern including a dimension of the at least two data points and a value range of the at least two data points, and
         determining the data type based on the data pattern,
            the data type being one of a plurality of available data types, and
         the determining the data type being performed by the computer device;
   determining, based on the data type, the visual representation of the data,
      the determining the visual representation being performed by the computer device; and
   causing, based on the linking the graphical element to the display component, the data to be displayed within the display component using the visual representation,
      the causing being performed by the computer device.
2. The method of claim 1, where the streaming data source includes a stored file.
3. The method of claim 1, where the determining the data type for the data further comprises:
   determining the data type based on a file header format associated with the streaming data source.
4. The method of claim 1, where the analyzing the read portion of the data to determine the data pattern includes:
   determining a first delimiter and a second delimiter included in the read portion of the data,
      where the first delimiter separates couplings, including the coupling, of individual data points, including the at least two data points, within the read portion of the data, and
      where the second delimiter separates the individual data points,
   determining, based on the first delimiter and the second delimiter, an organization of data points associated with the read portion of the data, and
   determining, based on the organization of the data points, the dimension of the at least two data points included in the coupling.
5. The method of claim 1, where the analyzing the read portion of the data to determine the data pattern includes:
   isolating a particular dimension of data from the read portion of the data,
   detecting an increasing variable in the isolated particular dimension of data,
   where the determining the data type based on the data pattern includes:
      selecting a one dimensional data type, from the plurality of available data types, based on detecting the increasing variable,
   where the determining the visual representation for the data includes:
      generating a graph that plots the data along the increasing variable, and
   where the causing the data to be displayed within the display component using the visual representation includes:
      causing the graph to be displayed within the display component.
6. The method of claim 1, where the analyzing the read portion of the data to determine the data pattern includes:
   determining that data, included in the read portion of the data, is arranged in three dimensions and is within a value range associated with a color scheme,
   where the determining the data type based on the data pattern includes:
      selecting a three dimensional data type, from the plurality of available data types, based on the data, included in the read portion of the data, being arranged in the three dimensions and within the value range associated with the color scheme, and
   where the causing the data to be displayed within the display component includes:
      causing a video to be displayed within the display component based on the data.
7. The method of claim 1, where the analyzing the read portion of the data to determine the data pattern includes:
   detecting video frames within the read portion of the data,
   where the determining the data type based on the data pattern includes:
      selecting a video data type, from the plurality of available data types, based on the detected video frames, and
   where the causing the data to be displayed within the display component includes:
      causing a video to be displayed within the display component based on the data.
8. The method of claim 1, where the analyzing the read portion of the data to determine the data pattern includes:
   determining that data, included in the read portion of the data, is arranged in three dimensions,
   where the determining the data type based on the data pattern includes:
      selecting a three dimensional data type, from the plurality of available data types, based on the data, included in the read portion of the data, being arranged in the three dimensions, and
   where the determining the visual representation of the data includes:
      generating a three dimensional graph based on the data.
9. The method of claim 1, where the analyzing the read portion of the data to determine the data pattern includes:

determining that data, included in the read portion of the data, is arranged in two dimensions,
where the determining the data type based on the data pattern includes:
selecting a two dimensional data type, from the plurality of available data types, based on the data, included in the read portion of the data, being arranged in the two dimensions, and
where the determining the visual representation of the data includes:
generating a two dimensional graph based on the data.

10. The method of claim 1, where the analyzing the read portion of the data to determine the data pattern includes:
detecting audio frames within the read portion of the data,
where the determining the data type based on the data pattern includes:
selecting an audio data type, from the plurality of available data types, based on detecting the audio frames, and
where the determining the visual representation of the data includes:
generating an audio stream based on the data, and
generating the visual representation based on the audio stream.

11. The method of claim 1, where the analyzing the read portion of the data to determine the data pattern includes:
detecting signal frames or control bits associated with diagnostics data,
where the determining the data type based on the data pattern includes:
selecting a diagnostics data type, from the plurality of available data types, based on detecting the signal frames or the control bits associated with the diagnostics data, and
where the determining the visual representation of the data includes:
providing a diagnostics window based on the data.

12. A computing device, in a technical computing environment, comprising:
a memory to store streamed data associated with a streaming data source;
a processor to:
receive a first graphical element, based on a user input and via the technical computing environment, for the streaming data source;
link, based on the user input and via the technical computing environment, the first graphical element to the streaming data source;
link the first graphical element to a second graphical element for displaying a visual representation of the stored streamed data;
read a portion of the stored streamed data,
the read portion of the stored streamed data including a group of data that includes at least two data points,
the group of data representing data to be displayed within the visual representation of the stored streamed data;
analyze the read portion of the stored streamed data to determine a data pattern,
the data pattern including a dimension of the at least two data points and a value range of the at least two data points;
determine a data type associated with the stored streamed data based on the determined data pattern,
the data type being one of a plurality of available data types;
generate the visual representation of the stored streamed data based on the data type; and
provide the first graphical element and the second graphical element for display,
the second graphical element including the visual representation of the stored streamed data, when provided for display, based on linking the first graphical element to the second graphical element.

13. The computing device of claim 12, where, when analyzing the read portion of the stored streamed data to determine the data pattern, the processor is to:
examine a file header format or a file extension associated with the stored streamed data.

14. The computing device of claim 12, where, when analyzing the read portion of the stored streamed data to determine the data pattern, the processor is to:
determine the dimension of the at least two data points; and
where, when generating the visual representation of the stored streamed data based on the determined data type, the processor is to:
generate an n-dimensional graph based on the stored streamed data, where n corresponds to the determined dimension.

15. The computing device of claim 12, where, when analyzing the portion of the stored streamed data to determine the data pattern, the processor is to:
detect one or more audio frames or one or more video frames associated with the stored streamed data; and
where, when generating the visual representation of the stored streamed data based on the determined data type, the processor is to:
generate a visual representation of an audio stream or a video stream based on the detected one or more audio frames or the one or more video frames.

16. The computing device of claim 12, where, when analyzing the portion of the stored streamed data to determine the data pattern, the processor is to:
detect one or more signal frames or one or more control bits associated with diagnostics data; and
where, when generating the visual representation of the stored streamed data based on the determined data type, the processor is to:
provide a diagnostics window based on the one or more signal frames or the one or more control bits.

17. One or more non-transitory computer-readable media storing instructions, the instructions comprising:
one or more instructions that, when executed by a processor, cause the processor to:
receive, via a technical computing environment, an input for associating streaming data with a graphical element;
receive the graphical element based on the input;
link the graphical element to a display component,
the display component for displaying a visual representation of the streaming data,
the display component and the graphical element being provided for display;
read a portion of the streaming data,
the read portion of the streaming data including a group of data that includes at least two data points,
the group of data representing data to be displayed within the visual representation of the streaming data;
analyze the read portion of the streaming data to determine a data pattern, the data pattern including a dimension of the at least two data points and a value range of the at least two data points;

identify a data type associated with the streaming data based on the determined data pattern, the identified data type being one of a plurality of available data types;

generate the visual representation of the streaming data based on the identified data type; and cause the generated visual representation to be displayed within the display component based on linking the graphical element to the display component.

18. The one or more non-transitory computer-readable media of claim 17, where the one or more instructions to analyze the read portion of the streaming data to determine the data pattern include:

one or more instructions to determine the dimension of the at least two data points; and where the one or more instructions to generate the visual representation of the streaming data include:

one or more instructions to generate an n-dimensional graph based on the streaming data, where n corresponds to the determined dimension.

19. The one or more non-transitory computer-readable media of claim 17, where the one or more instructions to analyze the read portion of the streaming data to determine the data pattern include:

one or more instructions to detect one or more audio frames or one or more video frames associated with the streaming data; and where the one or more instructions to generate the visual representation of the streaming data include:

one or more instructions to generate a visual representation of an audio stream or a video stream based on the one or more audio frames or the one or more video frames.

20. The one or more non-transitory computer-readable media of claim 17, where the one or more instructions to analyze the read portion of the streaming data to determine the data pattern include:

one or more instructions to detect one or more signal frames or one or more control bits associated with diagnostics data; and where the one or more instructions to generate the visual representation of the streaming data include:

one or more instructions to provide a diagnostics window based on the one or more signal frames or the one or more control bits.

\* \* \* \* \*